United States Patent
Gehring

(10) Patent No.: US 9,366,652 B2
(45) Date of Patent: Jun. 14, 2016

(54) BLOOD COAGULATION TIME DETERMINATION METHOD AND APPARATUS

(75) Inventor: Frank K. Gehring, Obernheim (DE)

(73) Assignee: ANDREAS HETTICH GMBH & CO. KG, Tuttlingen (DE)

(*) Notice: Subject to any disclaimer, the term of this patent is extended or adjusted under 35 U.S.C. 154(b) by 884 days.

(21) Appl. No.: 13/394,807

(22) PCT Filed: Sep. 9, 2010

(86) PCT No.: PCT/EP2010/005549
§ 371 (c)(1),
(2), (4) Date: May 27, 2012

(87) PCT Pub. No.: WO2011/029601
PCT Pub. Date: Mar. 17, 2011

(65) Prior Publication Data
US 2012/0252043 A1    Oct. 4, 2012

(30) Foreign Application Priority Data

Sep. 9, 2009 (DE) .......................... 10 2009 040 879

(51) Int. Cl.
*A61B 5/00* (2006.01)
*G01N 29/036* (2006.01)
*G01N 33/86* (2006.01)

(52) U.S. Cl.
CPC .............. *G01N 29/036* (2013.01); *G01N 33/86* (2013.01); *G01N 2291/0256* (2013.01)

(58) Field of Classification Search
CPC ....... G01N 33/86; G01N 33/4905; C12Q 1/56
USPC ................................. 600/369; 422/73; 435/13
See application file for complete search history.

(56) References Cited

U.S. PATENT DOCUMENTS 4,056,484 A * 11/1977 Heimburger et al. ............ 436/16
4,148,216 A *  4/1979 Do et al. ....................... 73/54.26
(Continued)

FOREIGN PATENT DOCUMENTS

EP       0215669 A2    3/1987
EP       0737853 A1    10/1996
(Continued)

OTHER PUBLICATIONS

Vikinge et al. Comparison of surface plasmon resonance and quartz crystal microbalance in the study of whole blood and plasma coaguulation. Biosensors & Bioelectronics 15 (2000) 605-613.*
Acoustics of Blood Plasma on Solid Surfaces, Marcus Andersen, Anders Sell Born et al., J. Biomater, Sci., Polymer Edn. vol. 13, No. 8, pp. 907-917 (2002).
Comparison of Surface Plasmon Resonance and Quartz Cystal Microbalance in the Study of Whole Blood and Plasma Coagulation, Biosensors & Bioelectronics 15 (2000) 605-613.
(Continued)

*Primary Examiner* — Etsub Berhanu
(74) *Attorney, Agent, or Firm* — Woodling, Krost and Rust

(57) ABSTRACT

The invention relates to a method for determining the coagulation time of a sample fluid containing blood components by means of a resonator whose vibration parameters are measured and then used as a basis for determining the sample fluid viscosity change, which resonator has an at least partially adhesive surface contacting said sample fluid. The invention is characterized by preincubation of said surface with a preincubation fluid containing blood components, which preincubation fluid has a known way of interacting with the coagulation system, thus resulting in anchoring sites to be formed on the adhesive areas of said surface.

7 Claims, 2 Drawing Sheets

(56) References Cited

U.S. PATENT DOCUMENTS

Figure 1:
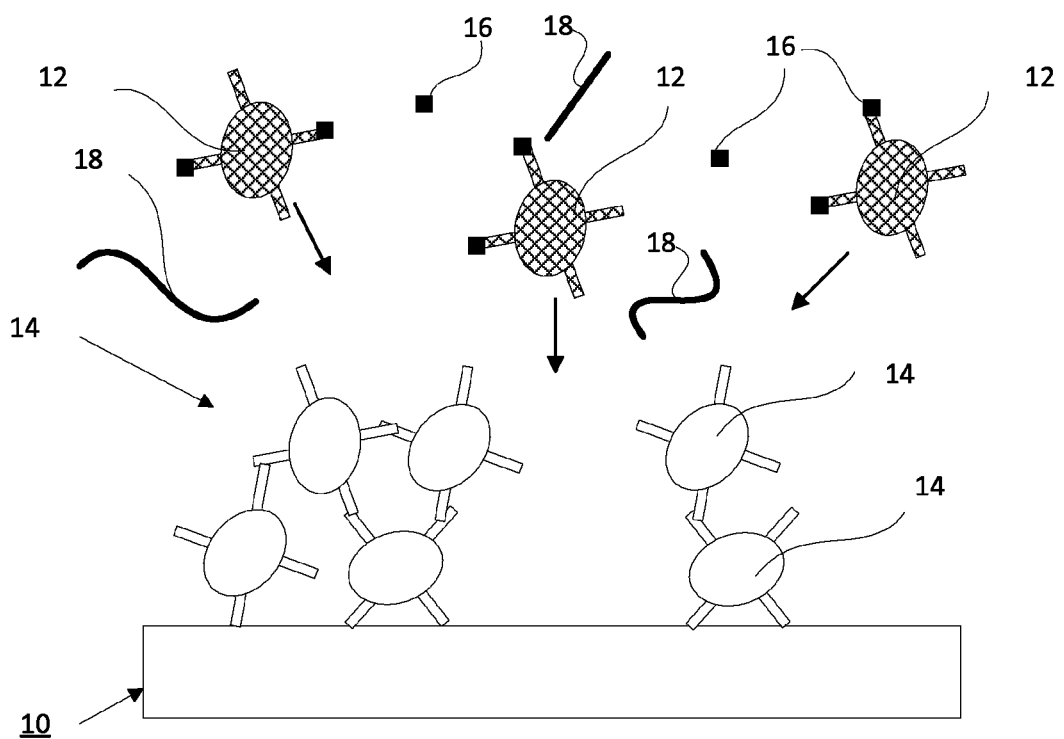

| | | | |
|---|---|---|---|
| 2005/0180887 A1* | 8/2005 | Sklar et al. | 422/73 |
| 2006/0051828 A1* | 3/2006 | Giesen et al. | 435/13 |
| 2007/0059695 A1* | 3/2007 | Lang | 435/6 |
| 2007/0154472 A1* | 7/2007 | Widom et al. | 424/133.1 |
| 2007/0178442 A1* | 8/2007 | Wienhues-Thelen et al. | 435/4 |
| 2008/0114549 A1 | 5/2008 | Schafer | |
| 2010/0081123 A1* | 4/2010 | Abbott et al. | 435/5 |

FOREIGN PATENT DOCUMENTS

| | | | |
|---|---|---|---|
| JP | 04032767 A | 2/1992 | |
| JP | 05164671 A | 6/1993 | |
| JP | 08075629 A | 3/1996 | |
| WO | 2004067130 A2 | 8/2004 | |

OTHER PUBLICATIONS

International Search Report, PCT/EP2010/005549, European Patent Office, Feb. 7, 2011.

English translation of International Preliminary Report on Patentability and Written Opinion of the International Searching Authority, Dated Mar. 22, 2012 (Mailing Date), PCT/EP2010/005549, International Bureau of WIPO, Applicant: Andreas Hettich GMBH & Co. KG., International Application Filing Date Sep. 9, 2010.

Berglin et al., The Effect of Substrate Molecular Mobility on Surface Induced Immune Complement Activation and Blood Plasma Coagulation, Biomaterials, vol. 25 No. 19, Elsevier Science Publishers BV, Aug. 1, 2004, p. 4581-4590, United Kingdom.

Japanese Patent Office, Notice for Reasons for Rejection, Office Action, Japanese Application No. 2012-528273, Mar. 10, 2014, p. 1-9.

* cited by examiner

BLOOD COAGULATION TIME DETERMINATION METHOD AND APPARATUS

This application is the national phase entry of PCT/EP2010/005549. This application claims the benefit and priority of and to PCT/EP2010/005549, international application filing date Sep. 9, 2010, which claims the benefit and priority of and to German patent application no. DE 10 2009 040 879.7, filed Sep. 9, 2009. PCT/EP2010/005549, international application filing date Sep. 9, 2010, and German patent application no. DE 10 2009 040 879.7, filed Sep. 9, 2009 are incorporated herein by reference hereto.

In emergency medical care or for monitoring patients with clotting disorders, the coagulation state or coagulability of a patient's blood is of vital importance. Clotting disorders usually have serious consequences for those affected. Both in the hypercoagulable and in the hypocoagulable state such consequences may be considerable. In general, coagulability is assessed using methods that allow a determination of what is called Quick's time. Historically, the further development of these methods has taken different forms.

A method which is especially attractive as regards technical potential is measuring the coagulation time using a quartz crystal microbalance. In this method, blood or plasma is applied to the quartz crystal microbalance surface and the frequency response or the damping behaviour is measured over time. As soon as a frequency drop by a certain extent has occurred, this indicates the coagulation time measured up to this point.

One example of this is disclosed in the printed document entitled "Comparison of Surface Plasmon Resonance and Quartz Crystal Microbalance in the Study of Whole Blood and Plasma Coagulation". Described in this document are general ways of measuring blood components using a quartz crystal microbalance. However, these methods are disadvantageous in that they do not allow a precise determination of the coagulation time, i.e. the time period from blood or plasma activation to a significant viscosity change. This makes these methods relatively inaccurate since they never determine a distinctive value of a curve but merely allow the coagulation time to be determined through a measurement with subsequent data processing.

Disclosed in the printed document entitled "Acoustics of Blood Plasma on Solid Surfaces" is the preincubation of a quartz crystal with citrated human plasma so as to saturate the non-specific binding sites. As a result, fibrin adsorption can be measured.

It is the object of the invention to provide a method which allows fast and precise determination of the blood coagulation time by means of a resonator.

This object is accomplished by contacting a quartz crystal with a preincubation fluid prior to application of a sample fluid. Anchoring sites are thus formed where coagulation is to take place. Owing to preincubation, blood components already become adsorbed to the adhesive resonator surface. In this manner, a layer of blood components is already formed. At a later stage in the process, this layer will facilitate the adsorption of further blood components, in particular the formation of a fibrin mesh, resulting in a viscosity change. It is thus ensured that coagulation will specifically occur near the quartz crystal surface and that the change in viscosity of the sample fluid resulting from coagulation can be measured promptly.

This method provides a fast, precise and versatile way of determining plasma coagulation parameters using only one apparatus which moreover has a vast miniaturisation and automation potential.

Prior to application of the sample fluid, the sample fluid can be mixed with an activator that will trigger coagulation. The activated sample fluid is then applied to the preincubated quartz crystal, with subsequent measurement of the vibration parameters of the resonators. Coagulation will occur near the quartz crystal surface since the activated blood components adsorb to the layer created by the preincubation.

In this way, the respective coagulation time can be determined within a matter of seconds. Without resonator preincubation there would always be some uncertainty in the determination of the coagulation time as the coagulation site cannot be influenced. The reason for this uncertainty is that—while the viscosity will change around the starting point of coagulation—such change will not yet be detected by the resonator owing to its distance from it and/or it cannot be detected due to the potential barrier layers. Preincubation with a fluid containing blood components thus exploits adsorption measurement characteristics that indicate what are actually parasitic effects occurring in viscosity measurements so as to obtain a higher degree of accuracy in determining the coagulation time.

In another step of the method, the resonator may be rinsed with a buffer solution following preincubation. Rinsing the resonator will ensure removal of any excess and/or unbound blood components that have adsorbed to the resonator. Furthermore, the surface of the resonators may be blown dry outside the measuring chamber after this step which in turn makes it possible to store the resonators. This allows the resonators to be first preincubated and dried, and only installed in a suitable measuring instrument when required.

Moreover, any excess unbound blood components in the measuring chamber or on the resonator surface will constitute an additional element of uncertainty. Rinsing off any excess blood components will eliminate this disturbance.

In a particularly advantageous mode, the preincubation fluid used for preincubating the resonator is identical to the sample fluid. This prevents coagulation factors that may not actually be contained in the sample fluid from being introduced through preincubation. The preincubation fluid may be whole blood, or a semi- or fully synthesized fluid containing blood components.

The term "blood components" as used in the context of the invention refers in particular to coagulation-relevant components such as thrombocytes and/or coagulation factors.

In particular, the resonance frequency is measured as a vibration parameter over time. Measuring the resonance frequency is particularly suitable for determining a change in viscosity since viscosity will already change noticeably at a low degree of adsorption. The coagulation time is determined by measuring the time period from sample fluid activation to a local frequency maximum in the resonance frequency curve. Alternatively, it is also possible to measure damping as a vibration parameter. In this case, the characteristic of the damping curve will be inverse to that of the resonance frequency.

Instead of determining a local maximum in the resonance frequency, or a minimum in the case of the damping, it is also possible to determine the inflection point. Whether the inflection point or a turning point is to be determined will depend on the surface coating of the resonator.

From this time value, i.e. the time period from sample activation to coagulation, and depending on the activator added, it can then be inferred that respective coagulation abnormalities exist in the sample fluid.

If the sample is activated using a calcium-thromboplastin solution for example, then the measured time period until coagulation occurs will correspond to the thromboplastin time which is also referred to as Quick's time in technical literature. Determining Quick's time is extremely important for patients under Marcumar® for example. If Quick's time is too long, these patients may be at risk of suffering internal bleeding.

On the other hand, if the sample fluid is activated through contact phase and phospholipids, the associated time period will correspond to aPTT which is another important factor in today's coagulation diagnostics.

Furthermore, the activated clotting time (ACT) can be measured. ACT is determined by activating the sample fluid with kaolin or silica. On the basis of the ACT in combination with the known number of thrombocytes an assessment can be made regarding the function of the endogenous coagulation system and the presence of disseminated intravascular coagulopathy (DC).

In addition to determining the coagulation time, it is also possible to determine the kinetics of the frequency and/or the damping curve, above all based on the function of the frequency as a function of the damping. This additionally allows a conclusion to be drawn as regards the clotting properties. This allows a more precise coagulation analysis.

Preferably whole blood or plasma is used as the sample fluid. Whole blood is primarily suitable for an analysis of the coagulation time of an emergency patient whereas plasma tends to be used in research.

A particularly advantageous mode allows the detection of hyperfibrinolysis. For this purpose, the vibration parameters are measured for a longer time than is required for determining the coagulation time. For measuring the coagulation time, a frequency drop or a damping increase is obtained. In the case of hyperfibrinolysis and/or fibrinolysis, this value will then reverse again.

Studies have shown that resonator preincubation for at least 15 seconds is particularly advantageous.

Furthermore provided is a method for measuring coagulation parameters which method can be used to determine hyperfibrinolysis by measuring at least one vibration parameter beyond the coagulation time. Hyperfibrinolysis shall then be assumed to be present if, following the coagulation time, a vibration parameter curve characteristic is detected that is opposite to the coagulation. If the vibration parameter monitored was the frequency, this means that a frequency drop could he observed during coagulation. If there is a frequency rise following coagulation, this suggests that hyperfibrinolysis is present. Analogously, if the damping curve drops after coagulation, the diagnosis will also be hyperfibrinolysis. This method may be performed subsequently to the method according to the invention which will allow vast savings in terms of time and money.

Furthermore, the invention provides an apparatus for measuring the coagulation time by means of a vibrating quartz crystal which allows a reliable and precise determination of haemostasis parameters.

As already set out above, it is generally known to determine the coagulation time using a vibrating quartz crystal having a surface facing the blood sample. In the prior art, however, there is the problem that, if the vibrating quartz crystal surface is completely protein- and/or cell-resistant, coagulation will not take place directly on the vibrating quartz crystal surface. In this case, measuring the viscosity change brought about by the coagulation will either not be possible at all or at least not yield valid results. In the case of an adhesive surface, the thickness of the adsorbed layer will affect the resonator to such an extent that no measurement will be possible anymore.

Particularly well suited for performing the inventive method is a vibrating quartz crystal whose surface has areas that are adhesive and areas that are non-adhesive as regards blood components.

This combination of adhesive and non-adhesive surface areas will yield the advantage that blood components will on the one hand be adsorbed to the adhesive areas and will bridge the non-adhesive areas by forming aggregates and fibrin meshes, on the other.

Contrary to the prior art, this is a reliable way of accomplishing coagulation directly on the vibrating quartz crystal surface, in which case the viscosity change caused by the coagulation will also be indicated by a useful sensor signal. This will ensure a reliable and precise measurement of plasmatic coagulation parameters.

In yet another advantageous embodiment of the invention, the non-adhesive areas are formed so as to be protein- and/or cell-resistant. This is advantageous in that the blood components will not be adsorbed to this surface. Where blood components adhere to a surface in an excessive amount, viscosity can no longer be measured since the viscosity will be masked by the adhesion.

In another particularly advantageous embodiment, the adhesive and non-adhesive areas are arranged in the form of a mosaic on the vibrating quartz crystal surface. Such a surface design allows particularly precise measurements to be performed.

In particular, the adhesive areas are made of gold and the non-adhesive areas are made of poly ethylene (PE). Using these materials for the surface is advantageous in that both gold and poly ethylene (PE) are very common materials in microsystems engineering and are thus well known and easy to process. Another advantage of using a gold layer is that it may simultaneously serve as an electrode of the vibrating quartz crystal.

In particular, the surface of the vibrating quartz crystal is subdivided such that the non-adhesive areas will occupy between at least 20 per cent and maximally 90 per cent of the total sensor surface. This range will yield the best results.

Another advantageous effect can be obtained if an activator such as thrombin has already been incorporated into the vibrating quartz crystal surface. Advantageously, sample activation and application to the vibrating quartz crystal can thus be accomplished very fast if not simultaneously. Also, the total apparatus can be of a simpler design since activated blood will not have to be supplied as fast as possible to the resonator through a system of ducts or the like. The blood components will be activated as they adhere to the activated layer—which will then trigger plasmatic coagulation. For example, this allows the coagulation time to be determined from the time of the blood application to the actual coagulation.

Further advantages, features and possible applications of the present invention will become obvious from the description which follows, in combination with the embodiment illustrated in the drawings. The invention will be described in more detail with reference to the drawings.

Figure 2:
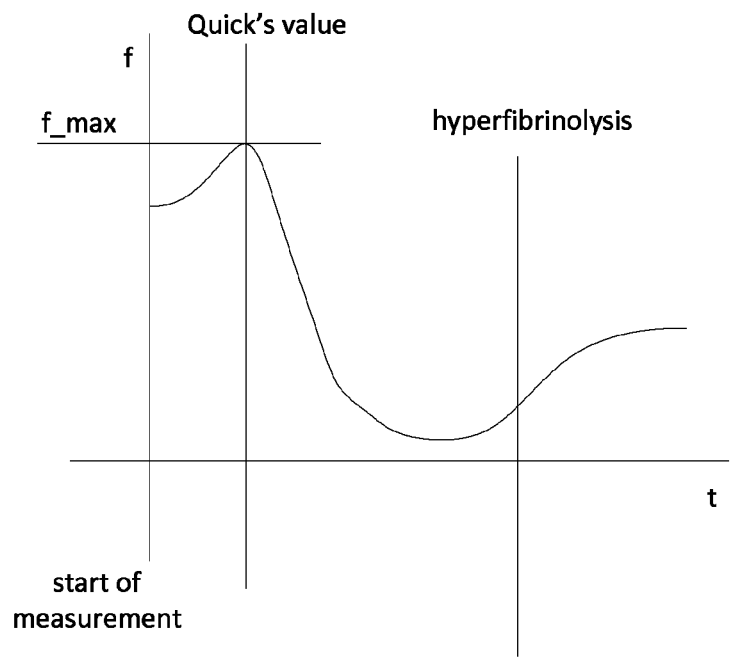
Figure 3:
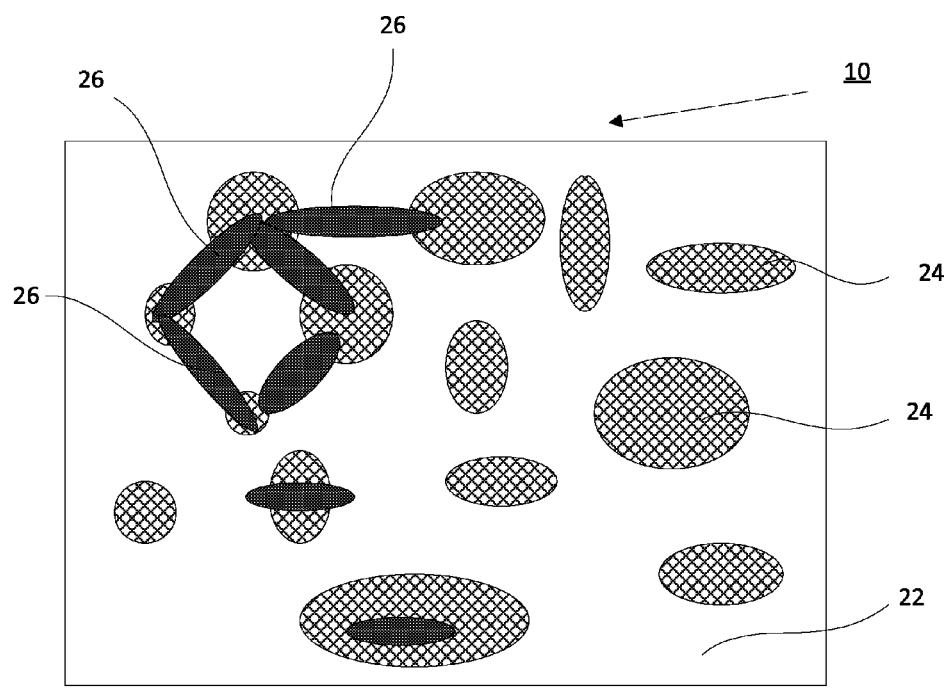

Throughout the description, claims and drawings, such terms and associated reference numerals will be used as are listed in the list of reference numerals below. In the drawings, FIG. 1 is an illustration of the adsorption of the blood components contained in the sample fluid on those of the preincubation fluid;

FIG. 2 is a graph of a resonance frequency for determining Quick's time (PTT); and FIG. 3 illustrates an apparatus having a vibrating quartz crystal surface made of PE and gold.

FIG. 1 shows a preincubated surface 10 of a resonator, with blood components 14 of the incubation fluid having become adsorbed to its adhesive surface as a result of preincubation. Furthermore, this drawing shows the blood components 12 of the activated sample fluid. The activator 16 will trigger coagulation.

In view of the already present anchoring sites, which were created by the blood components 14 of the preincubation fluid, the activated sample fluid will strive to trigger the plasmatic coagulation process at these sites that are located directly on the vibrating quartz crystal surface, e.g. through fibrin coupling. As—amongst others—a fibrin mesh will be formed in the case of an activated plasmatic coagulation, this will result in a viscosity change of the sample fluid directly on the vibrating quartz crystal surface and/or within the sensorially important penetration depth of the acoustic wave and can thus be easily detected by the resonator. This allows a very fast and accurate determination of the coagulation time.

FIG. 2 is a view of the frequency curve over time. The curve starts at the sample fluid application time. Sample fluid coagulation will have occurred once a local maximum of the curve is reached. Depending on the applicator used, this time period will correspond to a specific coagulation time, in this case to Quick's time, as a plasma thrombin solution was used.

In the further course of the curve one can see a sharp frequency drop. This indicates a continued increase in viscosity as a result of fibrin formation. Towards the end of the curve the frequency increases again which implies that hyperfibrinolysis and/or fibrinolysis is taking place and the fibrin formed during coagulation is thus being dissolved again.

FIG. 3 shows the surface of a vibrating quartz crystal 20 which includes a PE layer 22 and a gold layer 24. As is known, the PE layer 22 is cell-resistant. It thus prevents the adsorption of proteins and other cell components and blood components 26. The gold layer is adhesive by contrast and thus allows the adsorption of blood components 26 within this area. The blood components 26 bridge the non-adhesive PE areas 22. Due to the small number of possible adsorption sites, the layer of blood components will be of a thickness that will allow coagulation to occur directly on the vibrating quartz crystal surface. This arrangement yields a thin layer of blood components, which on the one hand ensures that coagulation occurs closely to the quartz crystal surface and, on the other hand, that the layer adsorbed to the surface will not be too thick and thus affect the vibration behaviour of the sensor.

Using the method set out above thus allows various coagulation times to be measured. The use of a vibrating quartz crystal allows a high degree of automation and a vast miniaturization potential.

LIST OF REFERENCE SIGNS

10 resonator
12 blood components of the sample fluid
14 blood components of the preincubation fluid
16 activator
18 fibrin
20 vibrating quartz crystal
22 PE layer
24 gold layer
26 blood components

The invention claimed is:

1. An apparatus for determining the coagulation time of a sample fluid containing blood components, comprising: a resonator, said resonator includes a surface, said surface of said resonator is a vibrating quartz crystal surface, said vibrating quartz crystal surface of said resonator includes non-adhesive areas (22) and adhesive areas (24) arranged in a mosaic on said vibrating quartz crystal surface, preincubation fluid containing blood components, said preincubation fluid (14) forming anchoring sites on said adhesive areas on said vibrating quartz crystal surface of said resonator, said adhesive areas of said vibrating quartz crystal surface of said resonator are adhesive with respect to said blood components of said sample fluid and said non-adhesive areas (22) of said vibrating quartz crystal surface of said resonator are non-adhesive with respect to aid blood components of said sample fluid, said vibrating quartz crystal surface of said resonator has a resonant frequency dependent on said sample fluid which engages and anchors to said anchoring sites on said adhesive areas of said vibrating quartz crystal surface of said resonator, and, said coagulation time occurs when said resonant frequency of said vibrating quartz crystal surface is at a maximum.

2. The apparatus of claim 1 wherein said non-adhesive areas (22) of said surface of said resonator are made as protein resistant and cell resistant.

3. The apparatus of claim 1 wherein said adhesive areas are formed of gold (24) and wherein said non-adhesive areas are made of polyethylene (22).

4. The apparatus of claim 1 wherein said non-adhesive areas (22) occupy between at least 20% and maximally 90% of the total vibrating quartz crystal surface.

5. The apparatus of claim 4 wherein an activator is incorporated into said vibrating quartz crystal surface.

6. The apparatus of claim 5 wherein said vibrating quartz crystal surface includes fibrinogen.

7. An apparatus for determining the coagulation time of a sample fluid containing blood components, comprising: a resonator, said resonator includes a surface, said surface of said resonator is a vibrating quartz crystal surface, said vibrating quartz crystal surface of said resonator includes non-adhesive areas (22) and adhesive areas (24) arranged in a mosaic on said vibrating quartz crystal surface, preincubation fluid containing blood components, said preincubation fluid (14) forming anchoring sites on said adhesive areas on said vibrating quartz crystal surface of said resonator, said adhesive areas of said vibrating quartz crystal surface of said resonator are adhesive with respect to said blood components of said sample fluid and said non-adhesive areas (22) of said vibrating quartz crystal surface of said resonator are non-adhesive with respect to said blood components of said sample fluid, said sample fluid containing blood components adhered to said adhesive areas and bridge said non-adhesive areas, said vibrating quartz crystal surface of said resonator has a resonant frequency dependent on said sample fluid which engages and anchors to said anchoring sites on said adhesive areas of said vibrating quartz crystal surface of said resonator, and, said coagulation time occurs when said resonant frequency of said vibrating quartz crystal surface is at a maximum.

* * * * *